United States Patent [19]

Jenkner

[11] 4,431,358

[45] Feb. 14, 1984

[54] APPARATUS FOR BREAKING UP STACKS OF BOARDS IN POWER SAWS OR THE LIKE

[76] Inventor: Erwin Jenkner, Lindenstrasse 13, D-7261 Gechingen (BRD), Fed. Rep. of Germany

[21] Appl. No.: 294,741

[22] Filed: Aug. 20, 1981

[51] Int. Cl.³ .............................................. B65G 59/02
[52] U.S. Cl. .................................. 414/114; 414/119; 414/100; 271/128; 271/130; 74/98; 74/107; 73/290 R; 200/61.42
[58] Field of Search .............. 271/128, 130, 152, 153, 271/154, 155, 143, 42; 414/114, 117, 118, 119, 100; 73/290 R; 74/98, 107; 200/61.18, 61.41, 61.42, 61.44

[56] References Cited

U.S. PATENT DOCUMENTS

| 3,040,911 | 6/1962 | Turner | 414/117 |
|---|---|---|---|
| 3,174,633 | 3/1965 | Stevens | 414/114 |
| 3,608,747 | 9/1971 | Shibata et al. | 414/114 |
| 3,888,364 | 6/1975 | Inoue et al. | 414/118 |
| 3,955,811 | 5/1976 | Gibson | 271/155 X |

FOREIGN PATENT DOCUMENTS 670517 7/1979 U.S.S.R. .............................. 414/119

*Primary Examiner*—Joseph E. Valenza
*Assistant Examiner*—Ken Muncy
*Attorney, Agent, or Firm*—Kontler, Grimes & Battersby

[57] ABSTRACT

Apparatus for breaking up stacks or boards in a power saw has a platform which carries a stack of boards and is movable upwardly by a motor which is automatically arrested in response to lifting of a preselected number of boards above a given level. The unit which effects the transfer of boards above such level onto a table which supports the boards during cutting carries a pivotable lever with an idler roller which rests on the topmost board during lifting of the platform, and the lever causes a switch or a signal comparing stage to arrest the motor for the platform when it assumes a preselected angular position. When the idler roller is moved off the topmost panel in response to transfer of the selected number of boards onto the table and resulting movement of the transfer unit relative to the platform, the lever assumes a given position in which it arrests the motor for the transfer unit. A master switch in the circuit of the motor for the platform is opened in response to lifting of the platform to a given maximum permissible level.

16 Claims, 7 Drawing Figures

APPARATUS FOR BREAKING UP STACKS OF BOARDS IN POWER SAWS OR THE LIKE

BACKGROUND OF THE INVENTION

The present invention relates to apparatus for breaking up or subdividing stacks of superimposed panels, particularly wooden or composition boards or sheets of plywood which must be fed into the range of a rotary saw blade in a power saw or an analogous machine tool. More particularly, the invention relates to improvements in power saws or analogous machine tools wherein a lifting device carries a stack of superimposed panels and cooperates with a transfer unit to supply desired numbers of superimposed panels or discrete panels into the range of the subdividing or severing tool.

In a machine tool of the above outlined character, it is necessary to control the extent of upward movement of the lifting device in order to ensure that a requisite number of panels will be placed into the range of the transfer unit, and it is further necessary to regulate the extent of back-and-forth movement of the transfer unit in order to reduce to a minimum the length of strokes of the transfer unit. As a rule, such operations are controlled by an attendant who stands or sits adjacent to a control panel with a variety of pushbuttons, knobs, levers or analogous actuating elements for the corresponding prime movers of the machine tool. The extent of upward movement of the lifting device must be changed whenever the operator desires to change the number of panels or boards which are to be moved into the range of the severing tool. In other words, it is necessary to monitor the number of panels which have been lifted into the path of movement of the transfer unit so that the latter can thereupon perform a working stroke and transfer the selected number of panels onto the table or another suitable work support of the machine tool. Analogously, it is necessary to monitor the length or width of the panels and to change the strokes of the transfer unit whenever the corresponding dimensions of the panels are changed to thus ensure that the transfer unit will perform return strokes whose length is just sufficient to enable the transfer unit to advance the selected number of superimposed panels (or a single panel) from the top portion of the stack on the lifting device onto the table (namely, into the range of the comminuting or severing tool) while the transfer unit performs its forward stroke.

The above outlined operations must be carried out by a conscientious operator in order to avoid damage to the workpieces and/or to parts of the machine tool, or injury to attendants. Furthermore, the work is time-consuming if the operator is not familiar with the operation of the controls because he or she is likely to cause the transfer unit to perform strokes of excessive length with attendant lengthening of intervals between successive severing operations.

OBJECTS AND SUMMARY OF THE INVENTION

An object of the invention is to provide a novel and improved apparatus which can be used in a power saw or an analogous machine tool to reduce the extent of or replace manual labor and to ensure reliable, reproducible and safe feeding of requisite numbers of workpieces into the range of one or more severing or other tools.

Another object of the invention is to provide such apparatus with novel and improved means for monitoring the levels of panels or boards which form a stack on the lifting device of a power saw or an analogous machine tool.

A further object of the invention is to provide the apparatus with novel and improved safety features which reduce the likelihood of damage to or destruction of the machine tool in the event of malfunctioning of the control means for accumulation of requisite numbers or groups of panels for transfer into the range of the severing tool or tools.

Still another object of the invention is to provide the apparatus with novel and improved means for automatically varying the length of strokes of the transfer unit when the length and/or width of the workpieces which constitute the stack is changed.

A further object of the invention is to provide a relatively simple and inexpensive apparatus which can be incorporated into or combined with existing power saws or analogous machine tools to enhance the safety and reliability as well as to increase the output of such machines.

A further object of the invention is to provide novel and improved remote-control means for one or more prime movers of a power saw or an analogous machine tool.

The invention is embodied in an apparatus for breaking up or subdividing stacks of panels in a power saw or an analogous machine tool into groups each of which contains a predetermined number (one or more) of panels. The apparatus comprises a lifting device (such as a horizontal platform which is movable up and down along suitable guide means) arranged to support a stack of superimposed panels, a table or an analogous work support which is adjacent to the lifting device and has an upper side or surface disposed at a predetermined level, an electric motor or other suitable prime mover means which is operable to move the lifting device upwardly so that the number of those panels of the stack on the lifting device which extend above the aforementioned predetermined level depends on the extent of upward movement of the lifting device, transfer means operable to shift those panels of the stack which are located above the aforementioned level onto the upper side of the support, sensor means which is arranged to rest on the topmost panel of the stack during upward movement of the lifting device so as to assume a plurality of different positions each of which corresponds to a different number of superimposed panels above the aforementioned level, and means for arresting the prime mover means for the lifting device in a predetermined position of the sensor means. The apparatus preferably further comprises means (such as a horizontal or substantially horizontal camshaft) for movably securing the sensor means to the transfer means so that the sensor means is compelled to share the back-and-forth movements of the transfer means between a retracted position in which the transfer means is ready to advance or transfer a requisite number of panels onto the support and an extended position in which the transfer of such panels is completed. In accordance with a presently preferred embodiment of the invention, the sensor means includes a lever which is pivotable with reference to the transfer means between a plurality of different angular positions, i.e., between a plurality of different positions of inclination with reference to the top face, surface or side of the lifting device.

In accordance with a further feature of the invention, the apparatus comprises second prime mover means (for example, a reversible electric motor) for moving the transfer means in a predetermined direction to thereby transfer panels from the stack onto the upper side of the support as well as counter to such direction. The sensor means is preferably located behind the transfer means, as considered in the aforementioned direction, and the sensor means or the transfer means can comprise a bearing for the aforementioned shaft and a rotary element (such as an idler roller) provided at the lower end of the lever and resting on the topmost panel of the stack during upward movement of the lifting device. Such rotary element reduces the likelihood of damage to or defacing of the topmost panel while such panel is engaged by the sensor means.

The arresting means for the prime mover means which moves the lifting device can comprise a rotary pinion, a toothed rack meshing with the pinion and connected with the lever so as to rotate the pinion between a plurality of angular positions in response to pivoting of the lever, and a switch or other suitable means for interrupting the operation of the prime mover means for the lifting device in a predetermined angular position of the pinion, such predetermined angular position of the pinion corresponding to the aforementioned predetermined position of the sensor means. The just discussed apparatus preferably further comprises means (such as a pivot pin) for articulately connecting the rack to the lever of the sensor means.

In accordance with a further feature of the invention, the aforementioned camshaft is rigidly connected to and is thus rotatable by the lever. The apparatus further comprises second prime mover means which is operable to move the transfer means in the aforementioned direction to transfer panels from the stack onto the upper side of the support as well as counter to such direction, cam means provided on and rotatable with the shaft and means (such as a switch in the circuit of the second prime mover means if the latter includes or constitutes an electric motor) for arresting the second prime mover means in a predetermined angular position of the lever. Such predetermined angular position is preferably different from the aforementioned predetermined position of the sensor means. The idler roller on the lever can be designed or positioned to move off the uppermost panel of the stack when the transfer unit has covered a certain distance on its way from the extended to the retracted position. This causes the cam on the camshaft to actuate the associated switch so as to trigger the operation of a delay unit which automatically arrests the second prime mover means as soon as the transfer unit reaches a position behind but preferably very close to the stack on the lifting device. This ensures that the operator need not change the stroke of the transfer unit because such stroke is changed automatically when the dimensions of panels constituting the stack on the lifting device are changed.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
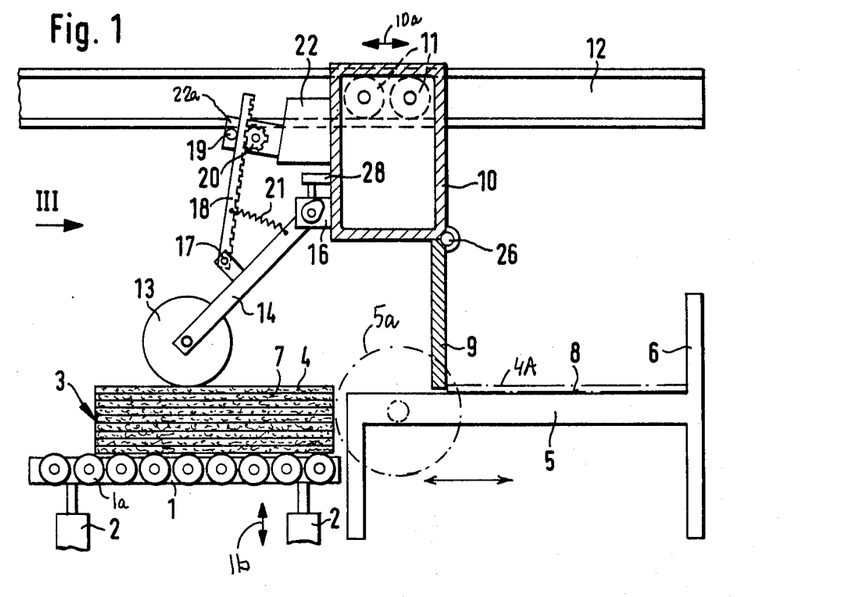
FIG. 1 is a schematic fragmentary partly elevational and partly vertical sectional view of an apparatus which embodies one form of the invention and is incorporated into a power saw wherein a rotary saw blade subdivides one or more panels into smaller panels, the sensor means of the apparatus being shown in a position it assumes during lifting of the stack of superimposed panels to a desired level.
Figure 2:
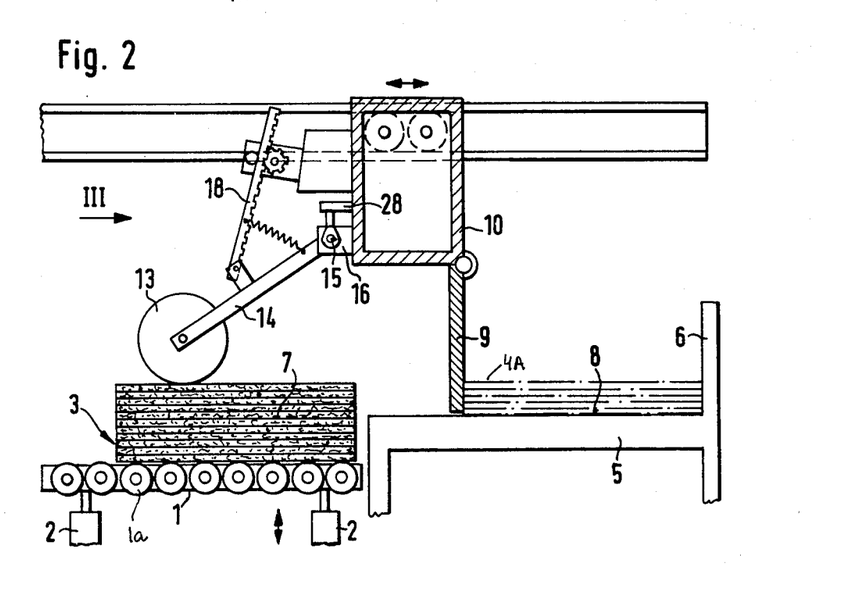
FIG. 2 illustrates the structure of FIG. 1 but with the lifting device shown at a different level so that several panels of the stack on the lifting device are located above the upper side of the table on which the panels rest during severing by the saw blade.
Figure 3:
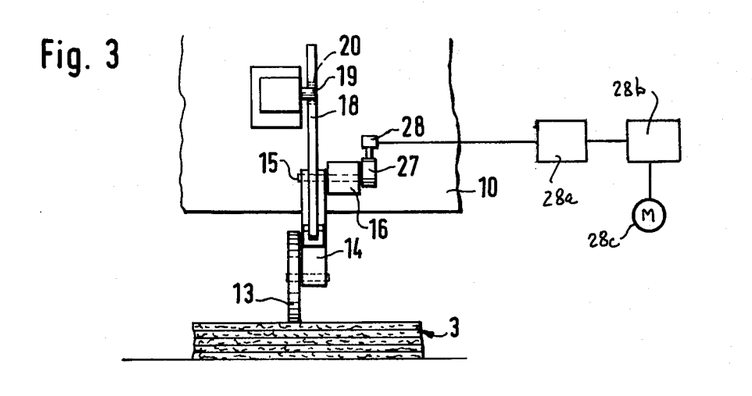
FIG. 3 is a fragmentary end elevational view of the apparatus, as seen in the direction of arrow III shown in each of FIGS. 1 and 2.

The apparatus of FIGS. 1 to 3 forms part of a power saw and comprises a lifting device 1 here shown as a platform with a plurality of rollers 1a which together define a top face for the underside of the lowermost panel or board 4 of a stack 3 of superimposed or overlapping panels. The lifting device 1 (hereinafter called platform for short) is movable up and down by a prime mover including two fluid-operated motors 2 whose piston rods are coupled to the platform and whose cylinders are attached to the floor or to the base of the power saw. The directions in which the motors 2 can move the platform 1 are indicated by a double-headed arrow 1b.

The platform 1 is movable up and down along a vertical path which is adjacent to a stationary table or support 5 having a horizontal upper side 8 and an upwardly extending stop 6 for one or more panels (one such panel is indicated in FIG. 1 by phantom lines, as at 4A). The severing or subdividing tool (e.g., a circular saw blade) is indicated at 5a; this tool is movable at right angles to the plane of FIG. 3 so as to sever the panel or panels (4A) on the upper side 8 of the table 5. When the saw blade 5a performs a working stroke, the panel or panels 4A abut against the stop 6 to ensure satisfactory orientation and subdivision of each panel into smaller sections or plates of predictable size and shape.

The apparatus further comprises a transfer unit which serves to deliver one or more superimposed panels 4 from the top portion of the stack 3 on the top face of the platform 1 (actually, on the apices of the rollers 1a) onto the upper side 8 of the stationary table 5. The number of superimposed panels 4 which are transferred while a pusher or entraining element 9 of the transfer unit performs a working stroke, namely, a movement in a direction to the right, as viewed in FIG. 1 or 2, depends on the level of the platform 1 at the time the pusher performs its working stroke, on the thickness of the panels 4 (all panels are assumed to have the same thickness) and on the height of the stack 3 on the platform 1. Thus, the pusher 9 will transfer all those panels 4 in the top portion of the stack 3 which are located above a predetermined level, namely, at or above the level of the upper side 8 of the table or support 5. The pusher 9 can comprise a single pivotable flap or a series of two or more aligned fingers which are pivotally connected to a crosshead or carriage 10 of the transfer unit by horizontal hinges 26 so that each finger can be readily pivoted counterclockwise, as viewed in FIG. 1 or 2, but cannot be pivoted clockwise beyond the position shown in FIG. 1 or 2. The carriage 10 has rollers or wheels 11 which track the lower flange of an elongated horizontal guide rail 12 so that the carriage can advance in directions indicated by a double-headed arrow 10a. The prime mover (e.g., a reversible electric motor) which drives the carriage 10 lengthwise of the guide rail 12 is shown in FIG. 3, as at 28c.

In FIG. 1, the underside 7 of the topmost panel 4 of the stack 3 on the platform 1 is located at the level of or slightly above the upper side 8 of the table 5. Thus, if the transfer unit is caused to perform first a return stroke (in a direction to the left, as viewed in FIG. 1), the fingers of the pusher 9 pivot slightly clockwise on engagement with the righthand edge face of the topmost panel 4 and thereupon slide along the upper side of such panel until after their tips move beyond such upper side so that each of the fingers can reassume its vertical or nearly vertical (illustrated) position before the carriage 10 begins to perform its forward stroke. During such movement of the carriage 10, the fingers of the pusher 9 entrain the topmost panel 4 from the stack 3 (the platform 1 is assumed to be at a standstill in the position shown in FIG. 1) and advance the topmost panel onto the table 5 so that the panel assumes the position 4A. The thus transferred panel 4A abuts against the stop 6 and the machine tool is ready to sever the panel 4A, i.e., the saw blade 5a is ready to move at right angles to the plane of FIG. 3. The manner in which the saw blade 5a is mounted, rotated and reciprocated in the frame including or supporting the table 5 forms no part of the present invention. Reference may be had to the commonly owned copending application Ser. No. 263,118, now U.S. Pat. No. 4,364,291, filed by me on May 13, 1981 for "Frame for a reciprocable circular saw".

FIG. 2 shows the platform 1 at a level such that a group of five topmost panels 4 of the stack 3 on the rollers 1a extends above the level of the upper side 8 of the table 5. A similar group of five superimposed panels 4A is shown on the table 5 and in positions of abutment with the stop 6. The fingers of the pusher 9 may but need not urge the panels 4A against the stop 6 while the saw blade 5a performs its cutting stroke. The underside of the fifth uppermost panel 4 in the stack 3 on the platform 1 of FIG. 2 is assumed to be located at the level of the upper side 8 of the table 5 or slightly above such upper side; it cannot be located below the level of the upper side 8 because this would prevent the pusher 9 from transferring five superimposed panels 4 while the fingers of the pusher perform a forward stroke, namely, toward the positions shown in FIG. 2. If desired, the apparatus of FIGS. 1 to 3 can have torsion springs, coil springs or other suitable means for yieldably biasing the fingers of the pusher 9 to the illustrated positions; such biasing means yield when the pusher 9 moves in a direction to the left, as viewed in FIG. 1 or 2, and the lower portions of the fingers strike against the right-hand edge face or faces of the panel or panels 4 extending above the level of the upper side 8. The guide rail 12 may constitute an I-rail and the carriage 10 may be provided with two sets of rollers or wheels 11, one set at each side of the web of the rail. This contributes to stability of the transfer unit, i.e., the carriage 10 is not likely to sway with reference to the guide rail 12. If the carriage 10 is relatively wide (see FIG. 3), the transfer unit can comprise two or more parallel guide rails 12 and the carriage 10 then comprises an equal number of sets of rollers or wheels 11, one set for each guide rail. The rollers or wheels 11 may constitute pinions and the flange or flanges of the rail or rails 12 then constitute toothed racks with which the pinions mesh. The prime mover 28c then constitutes a reversible electric motor which can rotate the pinions in a clockwise or in a counterclockwise direction, depending upon whether the pusher 9 is to be moved to the extended position of FIG. 1 or 2 or to the retracted position at the left-hand side of the stack 3, as viewed in FIG. 1 or 2. It is not necessary to drive all of the pinions, i.e., it suffices to rotate a single pinion or a single set of pinions or one pinion of each set. The remaining pinions then merely rotate in response to rotation of the driven pinion or pinions to thus ensure that the orientation of the carriage 10 with reference to the guide rail or rails 12 will remain unchanged.

As explained hereinabove, the platform 1 is raised to a desired extent (so as to move a selected number of topmost panels 4 of the stack 3 above the level of the upper side 8 of the table 5) before the motor 28c causes the pusher 9 to perform a return stroke toward a retracted position at the left-hand side of the stack 3, as viewed in FIG. 1 or 2. In order to ensure that the return stroke of the pusher 9 will not be unnecessarily long, i.e., that the carriage 10 is arrested as soon as or immediately or shortly after the pusher 9 advances beyond and to the left-hand side of the stack 3, as well as that the prime mover including the motors 2 is automatically arrested as soon as the topmost panel 4 of the stack 3 on the platform 1 reaches a preselected level, the apparatus comprises a sensor which, in the illustrated embodiment, is movably secured to the carriage 10 so that it shares the back-and-forth movements of the pusher 9 in the directions indicated by arrow 10a. To this end, the lower left-hand portion of the carriage 10, as viewed in FIG. 1 or 2, is provided with a bearing 16 for a horizontal camshaft 15 which is parallel to the pintle of the hinge 26 and articulately connects the sensor (namely, the upper end portion of an elongated lever 14) to the carriage 10. The shaft 15 is rigid with the lever 14, i.e., this shaft turns with reference to the bearing 16 and carriage 10 when the stack 3 on the platform 1 causes the lever 14 to pivot. The sensor further comprises a rotary element 13, here shown as an idler roller, which is rotatably mounted at the lower end of the lever 14. This roller comes into actual contact with the topmost panel 4 of the stack 3 and its peripheral surface can be readily machined, coated or otherwise treated in such a way that it does not damage and/or deface the topmost panel 4 of the stack 3 when the pusher 9 is caused to perform a return stroke. The sensor including the lever 14 and its roller or wheel 13 is located at the trailing end of (i.e., behind) the carriage 10 of the transfer unit, as viewed in the direction of movement of the pusher 9 toward the end position shown in FIG. 1 or 2.

An intermediate portion of the lever 14 has a lug for a pivot pin 17 which articulately connects the lever with the lower end portion of a toothed rack 18 which meshes with a pinion 20 on a housing 22 secured to the rear side of the carriage 10. An extension 22a of the housing 22 supports not only the shaft of the pinion 20 but also an idler roll 19 which constitutes a guide for and maintains the teeth of the rack 18 in mesh with the teeth of the pinion 20. A coil spring 21 is connected between the lever 14 and the toothed rack 18; this spring also ensures that the rack 18 remains in mesh with the pinion 20 in all angular positions of the lever 14. If desired, the spring 21 can be designed to bias the lever 14 in a counterclockwise direction, as viewed in FIG. 1 or 2, so as to urge the roller 13 against the topmost panel 4 of the stack 13 therebelow. Alternatively, the lever 14 can be weighted so that it tends to pivot in a counterclockwise direction, as viewed in FIG. 1 or 2, under the action of gravity.

Figure 4:
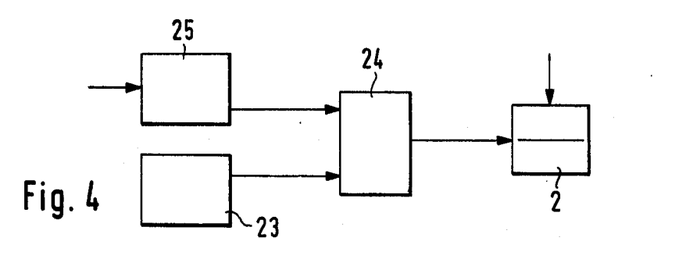
FIG. 4 is a circuit diagram of the arresting means for the motor means of the lifting device in the apparatus of FIGS. 1 to 3.

The angular position of the pinion 20 is monitored by a suitable monitoring device (shown at 23 in FIG. 4) which may constitute an angle encoder or a potentiometer and transmits signals denoting the momentary angular position of the lever 14 and hence the angular position of this lever with reference to the top face of the platform 1. The signals which are generated by the monitoring device 23 are transmitted to a first input of a signal comparing stage 24 which has a second input connected with the output of an adjustable source 25 of reference signals (e.g., a counter). The counter 25 can be installed in or at the control panel of the machine tool which embodies the structure of FIGS. 1 to 4, and the adjustment of the counter 25 will determine the number of panels 4 which are lifted above the level of the upper side 8 of the table 5 before the prime mover including the motors 2 is brought to a halt. As shown in FIG. 4, the output of the stage 24 is connected with such prime mover and the arrangement is such that the stage 24 transmits a signal which initiates stoppage of the prime mover for the plaftorm 1 when the signal which is transmitted by the monitoring device 23 matches the signal which is transmitted by the counter 25. Alternatively, the stage 24 can transmit a signal when the intensity or another characteristic of the signal from the monitoring device 23 deviates from the corresponding characteristic of the reference signal to such an extent that the difference is indicative of the lifting of a selected number of panels 4 above the level of the upper side 8 of the table 5.

The operation of the apparatus which is shown in FIGS. 1 to 4 is as follows:

The platform 1 is assumed to support a stack 3 consisting of a relatively large number of superimposed panels 4 (each such panel may constitute a wooden board or plank, a composition panel or a plywood panel). It is further assumed that the pusher 9 has completed a forward stroke and its fingers have completed the transfer of a selected number (e.g., five) of superimposed panels 4 from the top of the stack 3 on the platform 1 onto the upper side 8 of the table 5. The transferred panels abut against the stop 6 of the table 5 and are held in optimum positions for severing by the saw blade 5a. The carriage 10 then dwells in the position of FIG. 1 or 2, i.e., the prime mover 24c is idle and the pusher 9 bears or merely abuts against the left-hand edge face or faces of the transferred panel or panels 4A. The prime mover including the motors 2 is then started to lift the platform 1 while the roller or wheel 13 of the sensor including the lever 14 rests on the upper side of the topmost panel 4 forming part of the remaining portion of the stack 3. As the platform 1 rises, the angular position of the lever 14 with reference to the top face of the platform changes and the angular position of the pinion 20 changes accordingly because the pivoting lever 14 raises the rack 18 which, in turn, rotates the pinion 20. The angular position or the number of revolutions of the pinion 20 is monitored by the device 23 which transmits appropriate signals to the first input of the stage 24 while the second input of this stage receives the selected reference signal from the counter 25. When the intensities or other characteristics of the two signals are in a desired relationship with reference to each other, the stage 24 transmits a signal to arrest the prime mover including the motors 2 at the exact moment when the platform 1 has completed the lifting of a preselected number of panels 4 (e.g., five) above the level of the upper side 8 of the table 5.

The extent of upward movement of the platform 1 is selected by the attendant who is in charge of the control panel of the machine tool and has access to the adjusting means for the counter 25.

When the prime mover 2 is arrested, the motor 28c is started to move the carriage 10 in a direction to the left, as viewed in FIG. 1 or 2, whereby the pusher 9 pivots in a counterclockwise direction while its lower portion engages the top portion of the stack 3 on the platform 1. The pusher 9 is caused or allowed to pivot clockwise and back to the illustrated vertical position as soon as it has advanced beyond the upper side of the topmost panel 4 in the freshly lifted stack 3. In order to ensure that the transfer unit will be arrested as soon as the pusher 9 has moved beyond and to the left of the stack 3 on the platform 1, the aforementioned camshaft 15 which rotates in response to pivoting of the lever 14 carries a disc-shaped cam 27 which actuates a switch 28 (see also FIG. 3) in the circuit of a control unit 28b for the prime mover 28c. The connection between the switch 28 and the control unit 28b contains a suitable time-delay device 28a whose function is to delay stoppage of the prime mover 28c for a given interval of time which begins as soon as the lever 14 has caused the cam 27 to actuate the switch 28. The angular position of the cam 27 on the camshaft 15 is selected in such a way that the switch 28 is actuated as soon as the roller 13 advances beyond the upper side of the topmost panel 4 in the stack 3 and descends along the left-hand side of such stack, as viewed in FIG. 1 or 2. It is to be borne in mind that the roller 13 is leading when the carriage 10 moves in a direction to the left, as viewed in FIG. 1. The actuated switch 28 starts the time-delay device 28a (e.g., a suitable relay, a clockwork mechanism or the like) which actuates, with a given delay, the control unit 28b so that the latter arrests the motor 28c as soon as the pusher 9 advances past and descends along the left-hand side of the stack 3. This ensures that one need not monitor the width of the panels 4, as considered in the direction of forward or return movement of the carriage 10, because the arrangement which is shown in FIG. 3 automatically arrests the transfer unit at such a distance from the stop 6 that, when the pusher 9 reaches its retracted position, it is located at a given distance from the left-hand side of the stack 3 irrespective of whether the stack contains wide, very wide, narrow or very narrow panels. It will be noted that the angular position in which the lever 14 initiates stoppage of the prime mover including the motors 2 for the platform 1 need not be the same angular position in which the lever 14 causes the camshaft 15 (actually the cam 27 on the shaft 15) to actuate the switch 28 preparatory to stoppage of the prime mover 28c. As a rule, the time-delay device 28a will be adjusted or set in such a way that the motor 28c is arrested immediately or practically immediately after the pusher 9 moves beyond and to the left of the stack 3. This contributes to higher output of the machine tool because the length of intervals which are required to enable the transfer unit to perform its forward and return strokes is reduced to a minimum.

Figure 5:
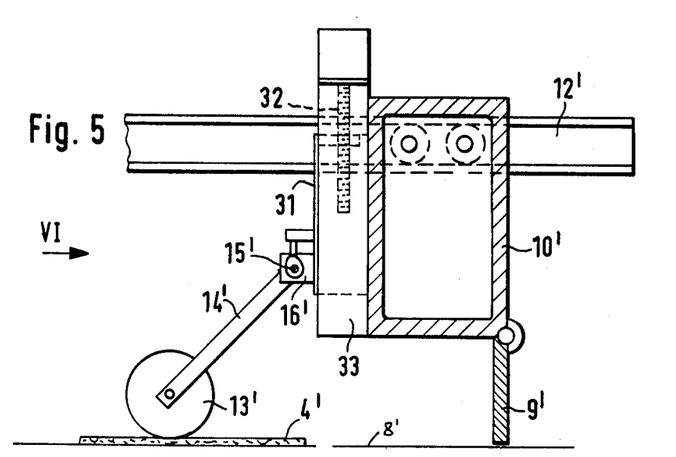
FIG. 5 is a fragmentary schematic partly elevational and partly vertical sectional view of a second apparatus.
Figure 6:
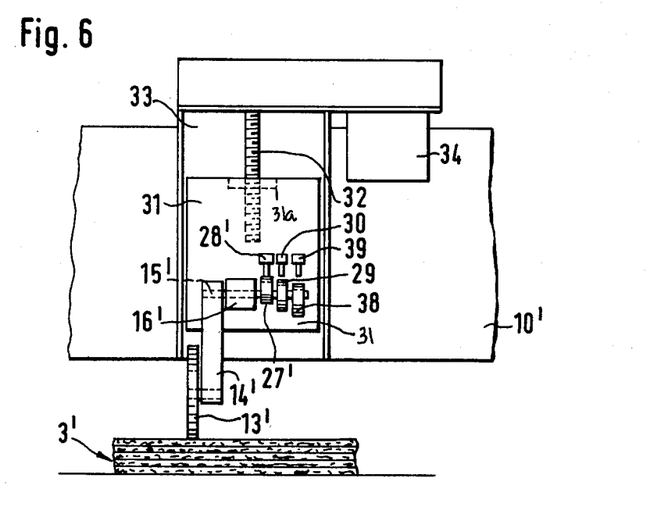
FIG. 6 is a fragmentary end elevational view as seen in the direction of arrow VI in FIG. 5.
Figure 7:
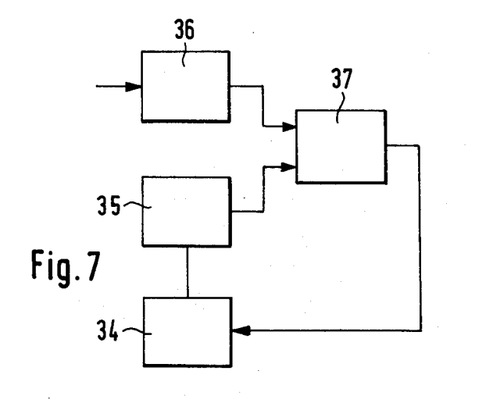
FIG. 7 is a circuit diagram of the means for changing the level of the sensor means in the apparatus of FIGS. 5 and 6.

Referring to FIGS. 5 to 7, there is shown a second embodiment of the improved apparatus wherein the roller 13' at the lower end of the pivotable sensor lever 14' again monitors the level of the topmost panel 4' of the stack 3' on the top face of the platform, not shown. The platform can be designed to move up and down in the same as described in connection with FIGS. 1 to 4. The difference is that the rack 18 and pinion 20 of the first apparatus are replaced with a second cam 29 on the camshaft 15' and a switch 30 which is actuatable by the cam 29 and arrests the prime mover (not shown) for the platform as soon as a preselected number of panels 4' has been lifted above the upper side 8' of the table. The camshaft 15' is rigidly connected with the upper end portion of the sensor lever 14' and is rotatable in a bearing 16' secured to the lower end portion of a plate-like member 31 forming part of means for adjusting the level of the shaft 15' and hence the extent of pivotal movement of the lever 14' before the cam 29 can trip the associated switch 30 in the circuit of the prime mover for the platform. The cam 27' on the camshaft 15' corresponds to the cam 27 of FIG. 3; this cam 27' cooperates with a switch 28' which corresponds to the switch 28 shown in FIG. 3, i.e., the cam 27' initiates stoppage of the prime mover for the carriage 10' of the transfer unit so that the rearward movement of the carriage 10' (namely, in a direction to the left, as viewed in FIG. 5) is terminated as soon as the pusher 9' moves beyond and to the left of the stack 3'.

In addition to the aforementioned plate 31, the adjusting means for selecting the level of the shaft 15' and hence the number of panels 4' which are lifted above the level of the upper side 8' of the table before the platform for the stack 3' is arrested comprises a vertical feed screw 32 which is rotatably journalled in a housing 33 of the carriage 10' and whose thread mates with the internal thread of a nut 31a secured to the upper portion of the plate 31. The angular position of the feed screw 32 is monitored by a potentiometer or a revolution counter 35 (shown schematically in FIG. 7) which transmits signals to the first input of a signal comparing stage 37. The second input of the stage 37 is connected with the output of a source 36 of reference signals, e.g., a counter in, on or at the control panel of the machine tool which embodies the structure of FIGS. 5 to 7. The counter 36 can be adjusted so as to determine that level of the camshaft 15' at which the change in angular position of the lever 14' with reference to the top face of the platform in response to lifting of the platform and of the stack 3' thereon suffices to ensure that a preselected number of panels 4' will be located above the level of the upper side 8' of the table whereby the lever 14' causes the camshaft 15' and the cam 29 to actuate the switch 30 which arrests the prime mover for the platform.

The stage 37 transmits signals to a prime mover 34 which is mounted on or in the carriage 10' and serves to rotate the feed screw 32 in a desired direction depending upon whether the attendant wishes to increase or reduce the number of panels 4' which are to be transferred onto the upper side 8' in response to each forward stroke of the pusher 9'. The manner in which the carriage 10' is mounted on and movable lengthwise of the guide rail or rails 12' is identical with or analogous to that described in connection with the carriage 10 and guide rail 12 in the apparatus of FIGS. 1 to 3.

FIG. 6 shows that the camshaft 15' carries a third disc-shaped cam 38 which can actuate a switch 39 in a preselected angular position of the lever 14', namely, in an angular position which is clearly indicative that the operative connection between the lever 14' and the prime mover for the platform is inoperative or that such prime mover is out of commission. The switch 39 is in circuit with the motor for the platform and, together with the associated cam 38, constitutes a safety feature which prevents excessive lifting of the stack 3', even in the event of malfunction of the prime mover for the platform and/or malfunctioning of the connection between the sensor means and such prime mover. A suitable time-delay relay or the like can be interposed between the master switch 39 and the control unit for the motor which lifts the platform. The switch 39 arrests the motor for the platform when the number of panels 4' above the level of the upper side 8' exceeds the preselected number.

The angular positions of the cams on the camshaft 15' are preferably adjustable. This enables an attendant to change the angular positions of the cams 27' and 38 on lifting or lowering of the plate 31.

An advantage of the second apparatus is that it embodies the aforediscussed safety feature (cam 38 and switch 39) as well as that a single component (camshaft 15') can initiate stoppage of the prime mover for the platform when a given number of panels 4' has been lifted above the level of the upper side 8', stoppage of the prime mover for the carriage 10' as well as stoppage of the prime mover for the platform in an emergency. Another advantage of the second apparatus is that the range of the lever 14' (insofar as the number of panels to be transferred is concerned) can be increased practically at will, depending on the extent of vertical adjustability of the plate 31 which carries the bearing 16' for the camshaft 15' and sensor lever 14'. In each of the illustrated embodiments, the number of panels in a group of panels to be transferred onto the table of the machine tool can be selected by remote control, and there is no need for continuous monitoring of the length or width of the panels 4 or 4' because the controls for the prime mover which drives the carriage 10 or 10' automatically arrest such prime mover as soon as the pusher 9 or 9' has moved beyond the stack 3 or 3' while the transfer unit was in the process of performing its rearward stroke, namely, away from the table for transferred panels.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for breaking up stacks of panels in a power saw or the like into groups containing predetermined numbers of panels, comprising a lifting device arranged to support a stack of panels; a table adjacent said device and having an upper side disposed at a predetermined level; first prime mover means operable to move said device upwardly so that the number of those panels of the stack on said device which extend above said level depends on the extent of upward movement of said device; transfer means operable to shift the panels above said level onto said upper side; sensor means arranged to rest on the topmost panel of the stack during upward movement of said device so as to assume a plurality of different positions at different levels each corresponding to a different number of panels above said level; means for movably securing said sensor means to said transfer means so that said sensor means is movable between said different levels with reference to said transfer means; means for arresting said prime mover means in a predetermined position of said sensor means; and second prime mover means for moving said transfer means with said sensor means in a predetermined direction to thereby transfer panels from the stack onto said upper side and counter to such direction, said sensor means being located behind said transfer means, as considered in said direction.

2. The apparatus of claim 1, wherein said sensor means includes a lever which is pivotable with reference to said transfer means.

3. The apparatus of claim 2, wherein said device has a top face and said lever is pivotable between a plurality of different positions of inclination with reference to said top face.

4. The apparatus of claim 1, wherein said sensor means comprises a lever, means for pivotably securing said lever to said transfer means, and a rotary element provided on said lever and resting on the topmost panel of the stack during upward movement of said device.

5. The apparatus of claim 4, wherein said lever has a first end portion pivoted to said transfer means and a second end portion, said rotary element constituting an idler roller on the second end portion of said lever.

6. The apparatus of claim 1, wherein said sensor means comprises a lever and means for pivotally connecting said lever to said transfer means, said securing means comprising a camshaft connected with and rotatable by said lever and further comprising cam means provided on and rotatable with said camshaft, and means for arresting said second prime mover means in a predetermined angular position of said lever.

7. The apparatus of claim 6, wherein said transfer means is movable to a position in which said sensor means is disengaged from the topmost panel of the stack on said device and said lever assumes said predetermined angular position in such position of said transfer means.

8. The apparatus of claim 7, wherein said securing means further comprises a bearing for said camshaft, said bearing being provided on said transfer means.

9. The apparatus of claim 1, wherein said sensor means comprises a lever and said securing means comprises a camshaft rotatable by said lever, said arresting means comprising a cam mounted on said camshaft and arranged to interrupt the operation of said first prime mover means in a predetermined angular position of said camshaft.

10. The apparatus of claim 1, further comprising means for adjusting the position of said securing means with reference to said transfer means.

11. The apparatus of claim 10, wherein said adjusting means includes means for moving said securing means up and down with reference to said transfer means.

12. The apparatus of claim 1, wherein said sensor means comprises a lever and means for pivotably securing said lever to said transfer means, said first prime mover means comprising an electric motor and said arresting means including a first switch in circuit with said motor and arranged to open in response to movement of said lever to a first predetermined angular position on lifting of a selected number of panels above said level, and further comprising a second switch in circuit with said motor and arranged to open said circuit in response to movement of said lever to a second predetermined angular position on lifting of a second number of panels above said level, said second number exceeding said selected number.

13. The apparatus of claim 12, further comprising second prime mover means arranged to move said transfer means in a direction to transfer panels from above said level onto said upper side and counter to such direction, and means for arresting said second prime mover means in response to disengagement of said sensor means from the topmost panel of the stack on said device.

14. Apparatus for breaking up stacks of panels in a power saw or the like into groups containing predetermined numbers of panels, comprising a lifting device arranged to support a stack of panels; a table adjacent said device and having an upper side disposed at a predetermined level; prime mover means operable to move said device upwardly so that the number of those panels of the stack on said device which extend above said level depends on the extent of upward movement of said device; transfer means operable to shift the panels above said level onto said upper side; sensor means arranged to rest on the topmost panel of the stack during upward movement of said device so as to assume a plurality of different positions each corresponding to a different number of panels above said level; means for movably securing said sensor means to said transfer means, said sensor means comprising a lever which is pivotable with reference to said transfer means; and means for arresting said prime mover means in a predetermined position of said sensor means, including a rotary pinion, a toothed rack meshing with said pinion and connected with said lever so as to rotate said pinion between a plurality of angular positions in response to pivoting of said lever, and means for interrupting the operation of said prime mover means in a predetermined angular position of said pinion.

15. The apparatus of claim 14, further comprising means for articulately connecting said rack to said lever.

16. Apparatus for breaking up stacks of panels in a power saw or the like into groups containing predetermined numbers of panels, comprising a lifting device arranged to support a stack of panels; a table adjacent said device and having an upper side disposed at a predetermined level; first prime mover means operable to move said device upwardly so that the number of those panels of the stack on said device which extend above said level depends on the extent of upward movement of said device; transfer means operable to shift the panels above said level onto said upper side; sensor means arranged to rest on the topmost panel of the stack during upward movement of said device so as to assume a plurality of different positions each corresponding to a different number of panels above said level; means for movably securing said sensor means to said transfer means, said sensor means comprising a lever and said securing means comprising a camshaft rotatable by said lever; means for arresting said prime mover means in a predetermined position of said sensor means, including a cam mounted on said camshaft and arranged to interrupt the operation of said prime mover means in a predetermined angular position of said camshaft; second prime mover means operable to move said transfer means in a direction to transfer panels from the stack on said device onto said upper side and counter to said direction; second cam means rotatable by said camshaft between a plurality of positions; and means for arresting said second prime mover means in a predetermined angular position of said second cam means, said predetermined angular position of said second cam means corresponding to a second predetermined position of said lever.

* * * * *